United States Patent [19]

Felsing

[11] Patent Number: 5,573,011
[45] Date of Patent: Nov. 12, 1996

[54] SYSTEM FOR QUANTIFYING NEUROLOGICAL FUNCTION

[76] Inventor: Gary W. Felsing, 133 Carlisle Way, Benicia, Calif. 94510

[21] Appl. No.: 224,939

[22] Filed: Apr. 8, 1994

[51] Int. Cl.$^6$ ........................................ A61B 5/10
[52] U.S. Cl. ........................................ 128/782
[58] Field of Search ........................ 128/774, 782; 33/1 N, 511, 512; 340/573, 686

[56] References Cited

U.S. PATENT DOCUMENTS

| | | | |
|---|---|---|---|
| 4,667,685 | 5/1987 | Fine | 128/782 |
| 5,058,571 | 10/1991 | Hall | 128/46 |
| 5,092,678 | 3/1992 | Chase et al. | 356/429 |
| 5,150,104 | 9/1992 | Thomas et al. | 128/782 |
| 5,313,968 | 5/1994 | Logan et al. | 128/782 |
| 5,337,758 | 8/1994 | Moore et al. | 128/781 |

OTHER PUBLICATIONS

Charcot, The Clinician: The Tuesday Lessons, p. 132, Jean Charcot, French neurologist Dec. 1883.
Kohl, Military Device Adapted for Use in Parkinson's, Neurology Reviews, Jul./Aug. 1993, p. 12.
Kolata, Parkinson Patients Set For First Rigorous Test Of Fetal Cell Implants, The New York Times Medical Science, Tuesday, Feb. 8, 1994, p. B8.
Tetrud et al., A Novel Device for Quantifying Tremor, Neurology Apr. 1993, vol. 43, No. 4, p. A410.
Dewhurst, "Characterisation of human . . . accelerometry." Med. & Biol. . . . Computing Jul. 1977.

*Primary Examiner*—Max Hindenburg
*Attorney, Agent, or Firm*—Wilson, Sonsini, Goodrich & Rosati

[57] ABSTRACT

A portable system for quantifying neurological function is described. The system comprises a gyroscope, power supply and signal analyzer. In one embodiment, the system includes a programmable computer, signal and power conditioning, signal analysis, memory and display capability. The angular rate sensed by the gyroscope is an output as a function of time and frequency. The power spectral density, Q, angular displacement, peak magnitudes and associated frequencies are obtained.

23 Claims, 7 Drawing Sheets

SYSTEM FOR QUANTIFYING NEUROLOGICAL FUNCTION

BACKGROUND OF THE INVENTION

The present invention generally relates to systems and methods for quantifying physical motion of humans and animals. In particular, the invention relates to systems and methods employing a gyroscope attached to a subject for quantifying the subject's neurological function.

Typically, neurologists make subjective visual evaluations of patients with neuromuscular disorders. Quantifying these motions has been difficult since they frequently are random and often involve the patient's extremities, such as the hands, feet, and head, where large and heavy sensors would alter the actual motion. It has been very difficult to adequately characterize the hand tremor resulting from Parkinson's disease and to identify early non-visible tremors.

Early attempts at quantifying this type of human motion were made in France in the 19th century by Charcot. He attached a short wand at one end to the hand and on the other end he fitted a small ink pen. As the hand shook, the pen recorded the motion on a piece of paper attached to the wrist. Neither frequency information nor calibrated output was available.

More current methods have employed mechanical linkages much like dentist drill arms having a potentiometer at each linkage joint. The motion of the extremity is indicated by the potentiometers. These linkages unduly restrict the motion of the physical extremity, can create backlash, hysteresis, and limit the measurements to those capable of being taken at a fixed location.

Later approaches have employed electromyographic (EMG) surface electrodes for tremor assessment. However, remote muscle activity and electrical interference can obscure the signal indicative of the tremor. Thus, EMG equipment cannot provide low noise tremor frequency information. Furthermore, the magnitude of the rate of movement and its angular displacement can not be obtained. Finally, EMG equipment is typically cumbersome and not easily portable.

Accelerometers have also been used but have a significant limitation in that they sense not only the acceleration of a hand tremor, for example, but also that from earth's gravitational field. A slight reorientation of the sensitive axis of the accelerometer with respect to the field can cause it to record an acceleration variation without any actual tremor. The actual tremor can not be distinguished from the perceived motion with one accelerometer.

Additionally, accelerometers small enough to not influence motion of a hand do not have a low enough frequency response (i.e. wherein the low corner of the frequency response coincides with DC) and do not have enough sensitivity. Conversely, accelerometers that do have the frequency response of interest (DC to 30 Hertz) are typically too large to be used.

Accelerometers are also very impractical to use when displacement information is required because of their bias errors. Bias error is the non-zero output of the accelerometer when there is no input. The first integration of the output to obtain the velocity of the motion will generate some error due to the bias error and due to any orientation shifts as noted earlier. A second integration to obtain the displacement makes the error even larger so that displacement really has not been accurately quantified. However, the gyroscope of the present invention yields an angular rate output that needs only a single integration to obtain angular displacement. This is a critical improvement. The gyroscope bias error is very small and unlike accelerometers, the gyroscope is not sensitive to orientation in earth's gravitational field for purposes of this application.

SUMMARY OF THE INVENTION

The present invention provides systems and methods of quantifying neurological function. It does this by utilizing one or more small solid state gyroscopes as the sensing elements. The output of the gyroscope has a frequency response from DC to approximately 70 Hertz, has a high degree of repeatability, and has high accuracy. Importantly, the gyroscope is essentially insensitive to earth's gravitational field. For example, the present invention allows a hand to move freely and without regard to orientation during measurement of hand tremor. The gyroscope will yield measurements completely unaffected by any position change.

In one embodiment of the present invention, the system includes a power supply providing regulated DC power to a gyroscope. The analog output signal from the gyroscope can be evaluated and displayed by a signal analyzer such as a Fast Fourier Transform (FFT) spectrum analyzer and/or recorded by a strip chart recorder.

In another embodiment, the system includes a programmable computer and an associated system module for power and signal conditioning. This computer based system supplies the gyroscope with regulated DC power, filters the analog voltage output of the gyroscope and provides the filtered output to a display and to an analog to digital (A/D) converter. The digital signal from the converter is processed in the computer to provide a FFT frequency spectral analysis, angular rate magnitude versus time plot, the sharpness of resonance (Q), and other parameters such as peak frequency, peak magnitude, and angular displacement. This type of information can be displayed on a monitor and/or in printed form for review by a neurologist, physical therapist, or research scientist.

DESCRIPTION OF THE PREFERRED EMBODIMENTS

Figure 1:
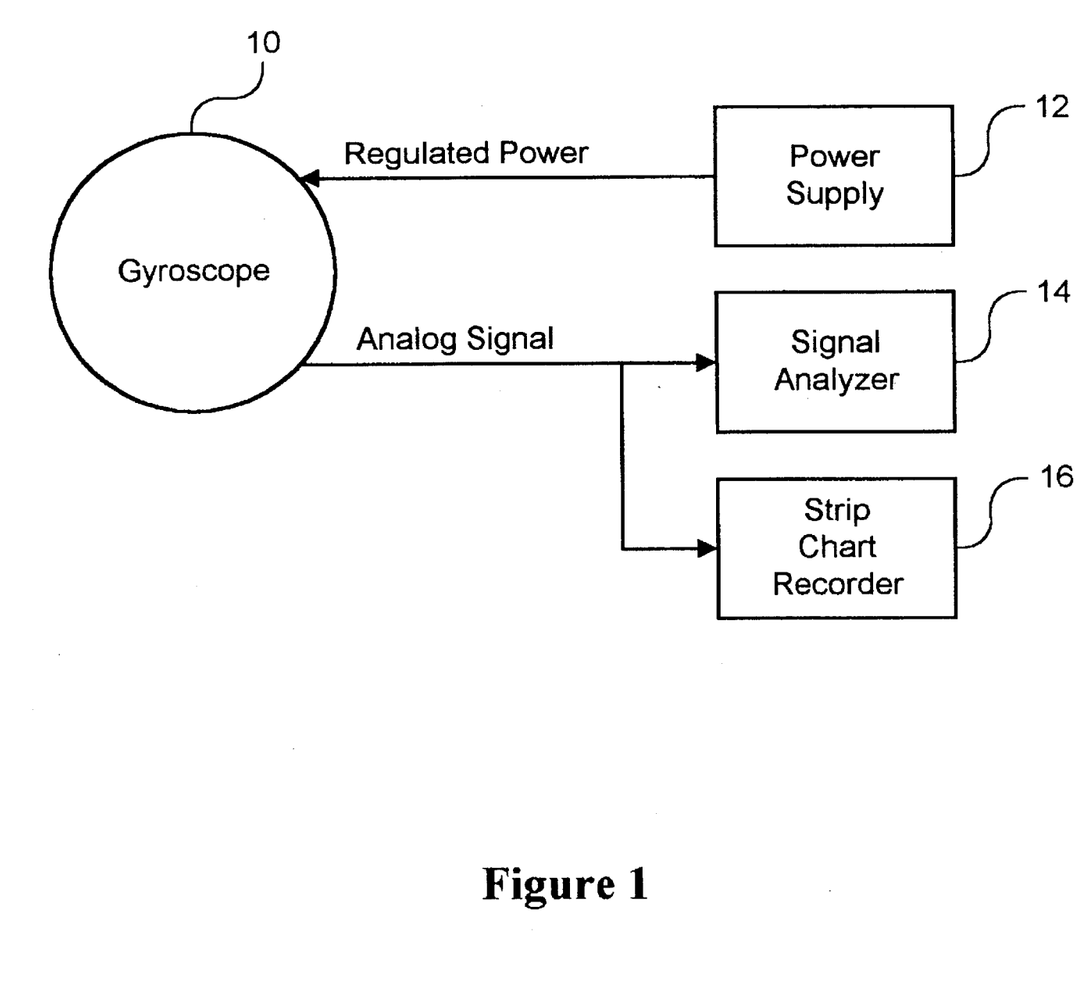
FIG. 1 is a block diagram of one embodiment of the system for quantifying neurological function.

FIG. 1 illustrates one embodiment of a system to quantify neurological function and other human or animal motions. As shown in the block diagram, the system provides a power supply 12 supplying regulated DC power to a gyroscope 10. The analog output signal from the gyroscope 10 can be evaluated and displayed by a signal analyzer 14 such as a Fast Fourier Transform spectrum analyzer and/or recorded by a strip chart recorder 16.

The gyroscope 10 is used to sense motion accurately over a range of frequencies, temperatures and time. It must be small and light in order to allow the hand or other extremity to move naturally and not be restricted by the bulk or mass of the gyroscope 10. Favorable results have been achieved by using a small solid state gyroscope manufactured by Systron Donner, Concord, Calif., such as the Systron Donner Model No. QRS 11. This gyroscope has excellent performance and is small enough to be used in these applications. The Model No. QRS 11 gyroscope is a right circular cylinder, is approximately 1.5 inches in diameter, 0.6 inch high and weighs under 60 grams.

In one preferred embodiment, the gyroscope 10 uses a micro-machined oscillating quartz tuning fork as a Coriolis sensor for detection of inertial angular rate. This tuning fork drives another quartz tuning fork which produces an internal signal (not shown) in the gyroscope 10. Electronics inside the gyroscope 10 demodulate the internal signal and provide an analog signal proportional to the angular rate of the motion. Because the gyroscope 10 does not use an acceleration sensitive methodology, it is inherently insensitive to its orientation in earth's gravitational field. In addition, since the gyroscope 10 is an inertial device, it can sense the inertial angular rate of motion without being tied to a fixed reference. This not only eliminates the need for mechanical linkages to connect the patient's extremity to stationary laboratory equipment, but also greatly simplifies operation and calibration.

Figure 2:
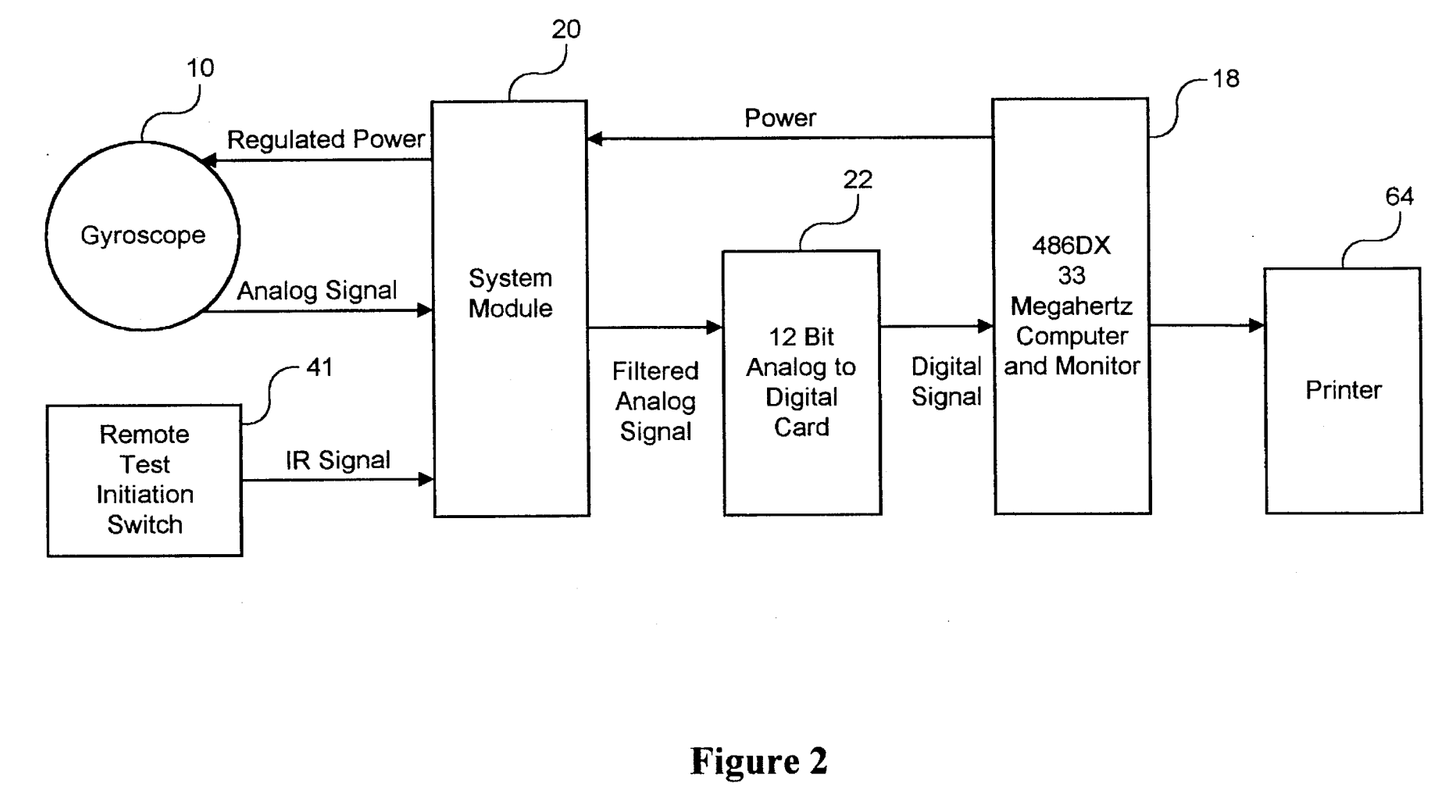
FIG. 2 is a block diagram of another embodiment of the system for quantifying neurological function.

The Systron Donner gyroscope operates off regulated plus and minus 5.0 volts DC. However, other gyroscopes could require other voltage levels. Thus, the voltage level is not crucial as long as it matches the requirement of the gyroscope used. The output signal of the Systron Donner gyroscope is between plus and minus 2.5 volts with zero volts being equal to zero angular rate. The input power can be supplied by a conventional power supply 12 in the system illustrated in FIG. 1 or by the system module 20 described in the system illustrated in FIG. 2.

Because tremors and other movements vary significantly in magnitude two ranges of angular rate are generally desired. For example, for measuring typical Parkinson's tremors, a gyroscope having a range of up to 100 degrees per second is appropriate, while measuring pronation/supination rotation of the arm may require a range of up to 1250 degrees per second. Likewise, two or more gyroscopes having substantially the same range are often desired to evaluate relative motion of bodily extremities.

Figure 3:
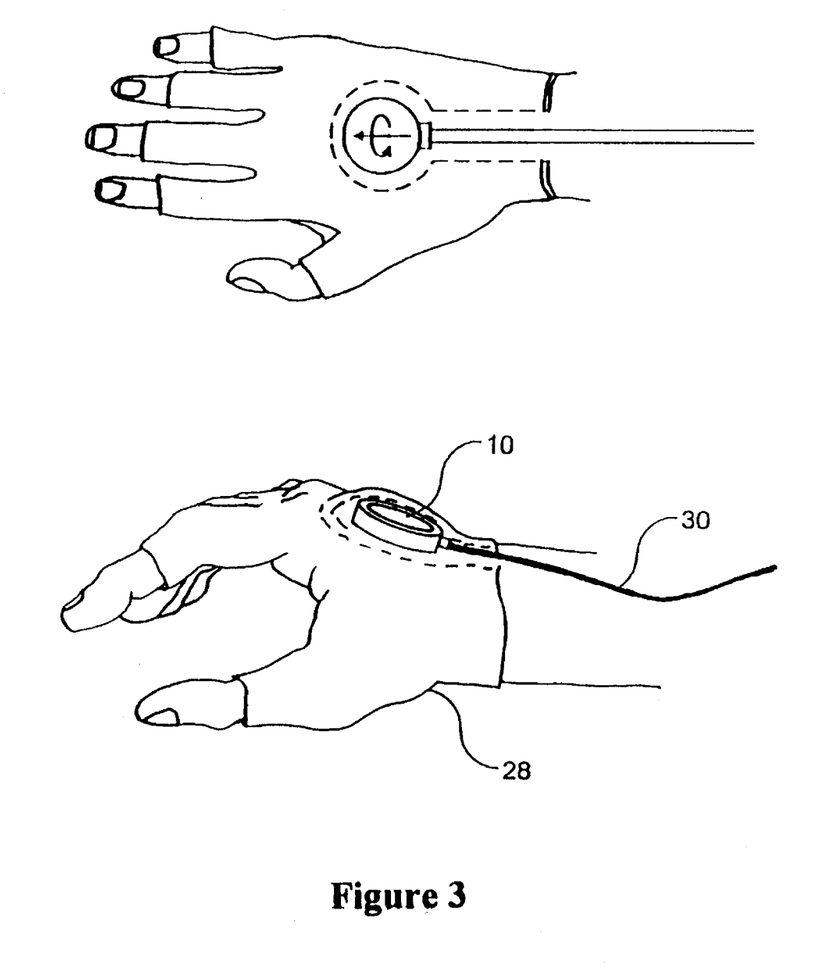
FIG. 3 illustrates a gyroscope mounted to a patient's hand while quantifying neurological function such as Parkinson's tremor.

As shown in FIG. 3, the gyroscope 10 is firmly held to the subject by tape or elastic glove 28 with the sensitive axis generally oriented parallel to the longitudinal axis of the extremity so that rotation about that axis is measured. Experimental work has shown that many types of tremors are in fact primarily rotational and best quantified in this manner. The gyroscope 10 is connected to the system module 20 (discussed below) associated and preferably located in the computer 18, by a flexible electrical wire 30 so as to not restrain the rotation.

In one embodiment of the system illustrated in FIG. 1, the output of the gyroscope 10 is processed by a Hewlett Packard Model No. 35660A Dynamic Signal Analyzer (FFT) 14 and can be also supplied to a Astro-Med Dash IV Strip Chart Recorder 16.

Figure 4:
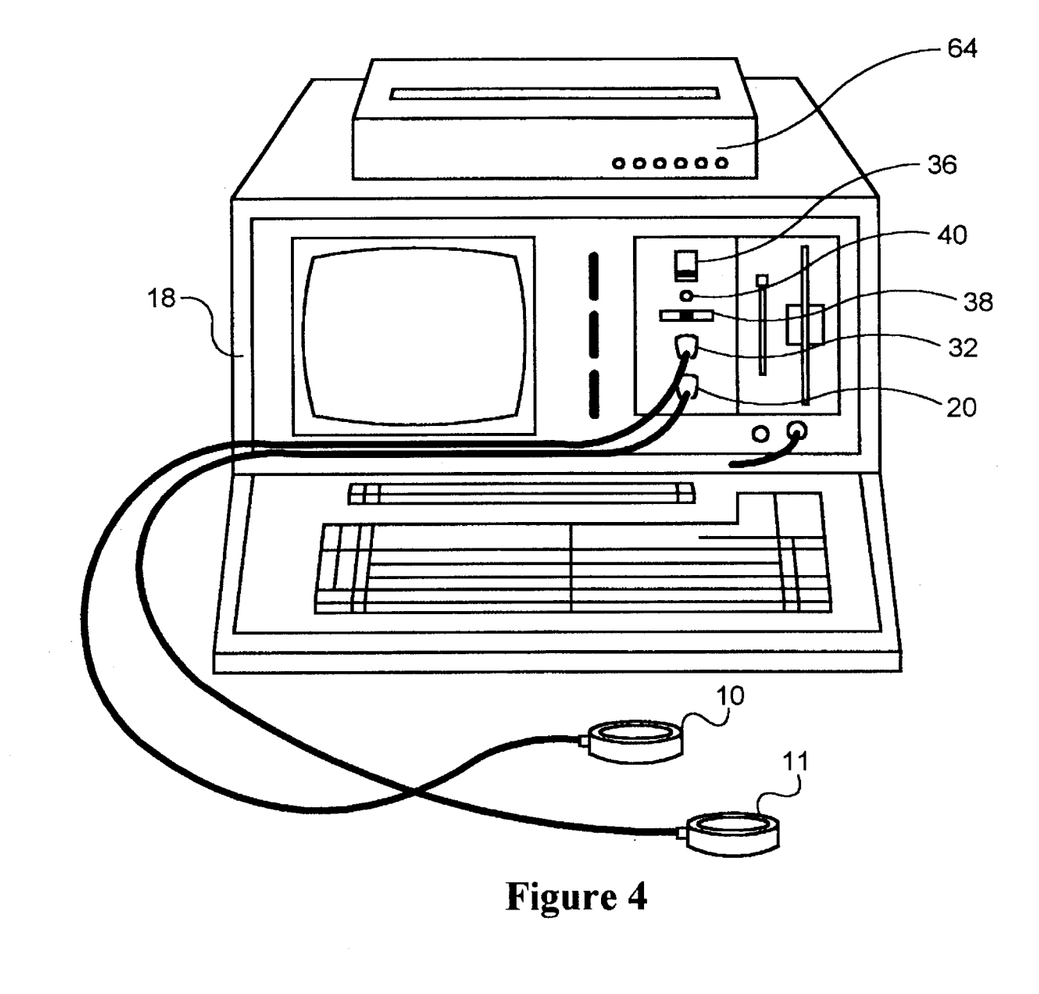
FIG. 4 is a perspective view of a portable embodiment of the system for quantifying neurological function.
Figure 5:
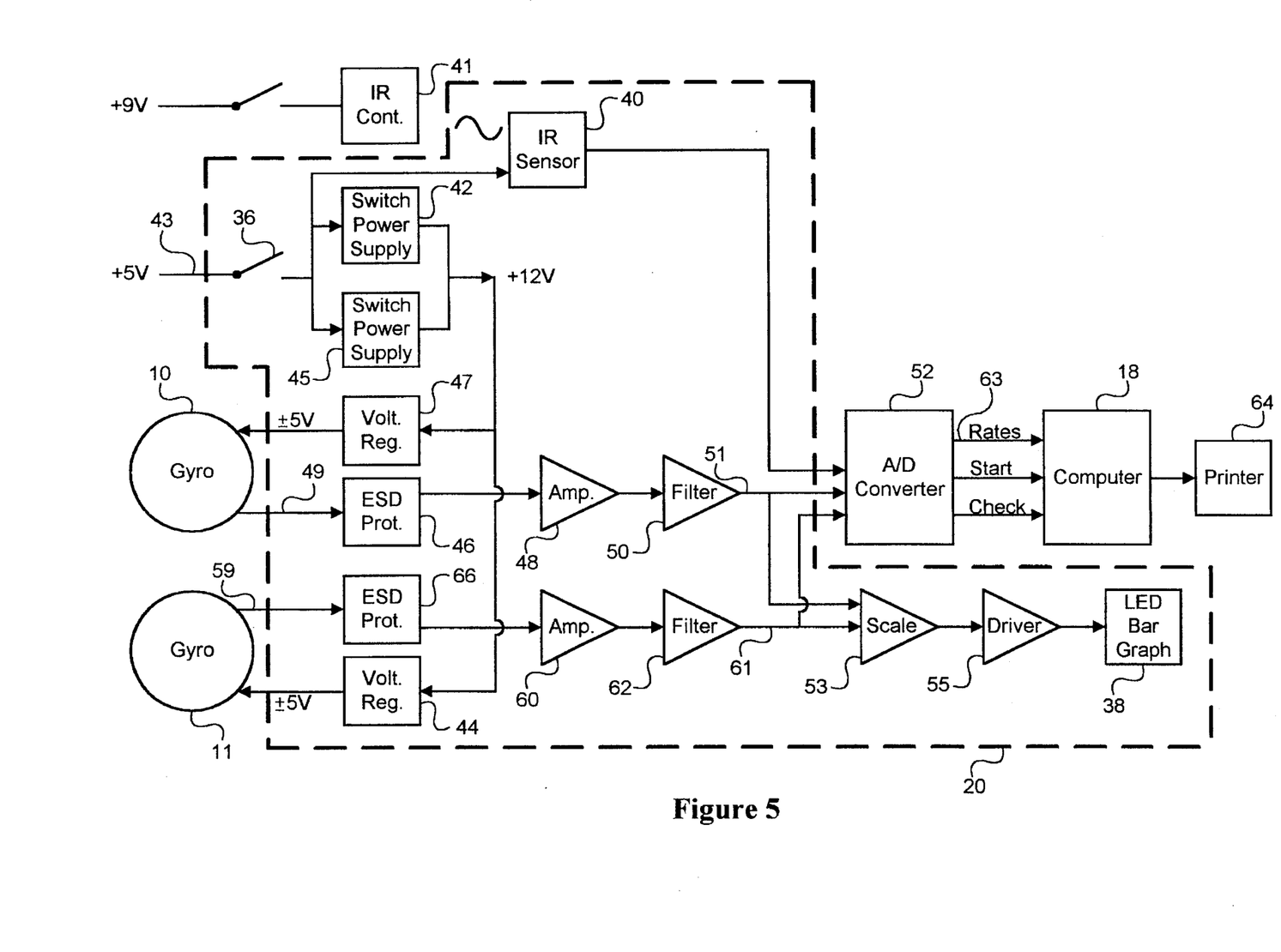
FIG. 5 is a detailed schematic of one embodiment of the system.

In another embodiment illustrated in FIGS. 4–5, these functions are contained within a portable computer 18 where its system module 20 provides the power and signal conditioning for the gyroscope 10, mating connectors 32 for one or more gyroscopes 10, 11 an on/off switch 36, a light emitting diode (LED) bar graph display 38 of the real time angular rate being sensed, and an infrared sensor 40.

The LED display 38 allows the operator to visually confirm that the gyroscope 10 is working properly since rotating the gyroscope 10 about its sensitive axis causes the illuminated bar of the display 38 to move back and forth as a function of how fast the gyroscope 10 is rotated. Because the display 38 and computer 18 are connected in parallel to the gyroscope 10, the display 38 can be used to help diagnose whether the gyroscope 10 or computer 18 is the source of a system malfunction. A ten segmented LED display such as Radio Shack Part No. RS276-081 is suitable for the display 38.

In a preferred embodiment, the system includes an infrared sensor 40 such as Radio Shack Part No. RS276-137 which is on front of the system module 20 which permits remote control of the system. This sensor 40 can be used in conjunction with a remote controller 41, including an infrared diode such as Radio Shack Part No. RS276-143, to initiate a test when a button on the controller 41 is pressed. This allows a busy physician to fully attend to the needs of his patient without constantly running back and forth to initiate tests at the computer 18.

FIG. 5 is a schematic illustrating an embodiment of the system, including switching power supplies 42, 45 preferably located in the system module 20. The power supplies 42, 45 convert an input of plus 5 volts from the computer power bus 43 to plus and minus 12 volts output. The plus 5 volt line from the computer 18 is suitable because of its excess power capacity. In one embodiment, the low end of power supply 42 is connected to the upper end of power supply 45. The output from the switching power supplies 42, 45 is regulated by one or more voltage regulators to plus and minus 5 volts. To prevent cross talk between two or more gyroscopes, each gyroscope should have its own set of voltage regulators. FIG. 5 illustrates one suitable arrangement where gyroscope 10 is coupled to Panasonic Part Nos. 7805 and 7905 voltage regulators 47 and another gyroscope 11 is coupled to Panasonic Part Nos. 7805 and 7905 voltage regulators 44. One source for the power supplies is Lambda Electronics Part No. AS3125, manufactured by Lambda Electronics, Melville, N.Y.

The output signal 49 of gyroscope 10 is protected against electrostatic discharge by conventional ESD circuitry 46, such as 1N4148 diodes. The signal is then amplified by a differential amplifier 48 and filtered by a 30 Hertz low pass second order filter 50 using the National Semiconductor Part No. LF412CN dual JFET op amp. The filter 50 is set at 30 Hertz since the gyroscope 10 bandwidth extends to 70 Hertz and human and animal motion of interest is typically under 20 Hertz. The filter 50 is located in the system module 20 and ensures a clean output signal 51 indicative of even very small preclinical tremors. This filtered output signal 51 is sent to an A/D converter 52 for further processing and can be also sent to a panel display meter scaling amplifier 53 using the National Semiconductor Part No. LF412CN dual JFET op amp and then to National Semiconductor Part No. LM3914N meter driver 55, and to the bar graph display 38. The output 59 of gyroscope 11 is protected against electrostatic discharge by conventional ESD circuitry 66, such as by 1N4148 diodes, and processed by differential amplifier 60 and a 30 Hertz low pass second order filter 62 using the National Semiconductor Part No. LF412CN dual JFET op amp, then to the A/D converter 52 for processing and to the panel display meter scaling amplifier 53, the meter driver 55, and to the bar graph display 38.

In one embodiment, the system module 20 can be housed in a sheet metal enclosure that fits within a portable or desk top computer disk drive bay. In the embodiment having two gyroscopes 10, 11, the system module 20 supplies the respective output signals 51, 61 to a 12 bit A/D converter 52 that converts the analog signals 51, 61 to digital signals 63. A 12 bit A/D converter was selected to provide resolution of about 0.2 degree/second for one bit of information where 12 bits are representative of 1000 degrees per second. An A/D converter having greater than 12 bits will improve the resolution but this has a cost penalty. Favorable results have been achieved when the A/D converter used is the Keithley Metrabyte Model No. DAS 802, manufactured by Keithley Metrabyte, Tauton, Mass.

The digital output signal representative of the gyroscope angular rate 63 can be further processed by software in a portable 486DX 33 megahertz computer 18. A computer having less computational power and slower clock speeds could be used, but would lengthen computational time. Software to perform such computations and display the results in graphical form is available from Keithley Metrabyte, Tauton, Mass. One suitable software package is VIEWDAC. In one embodiment, the computer includes a 212 MB hard disk drive, one 1.2 MB floppy drive (5.25 inch), one 1.4 MB floppy drive (3.5 inch) and a SVGA color card with 9.5 inch color monitor. The monitor should have a resolution capability of 1024 by 768 pixels. The computer should include at least 4 MB of RAM memory and has the Microsoft Corporation MS-DOS 6.0 version operating system. In an alternative embodiment, the computer could also include a graphical user interface such as Microsoft Corporation Windows 3.1 version.

Figure 6A:
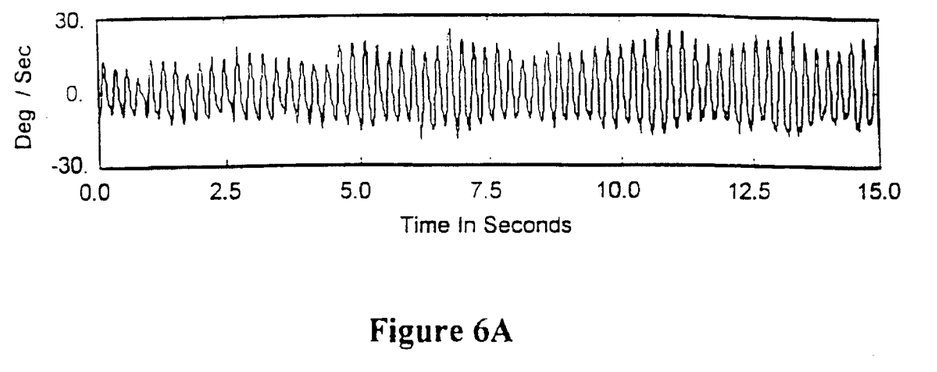
FIG. 6A illustrates a plot of angular rate versus time for a Parkinson's tremor which may not be visible to a trained neurologist.

The present invention provides frequency and time domain information of the angular rate of motion and other motion parameters of interest. FIG. 6A shows the angular rate (degrees/second) of a hand tremor indicative of Parkinson's disease as a function of time. The test is conducted for a 15 second period. This tremor has a very small angular rate of motion with a peak value of approximately 25 degrees per second and may not be visible to most neurologists.

Figure 6B:
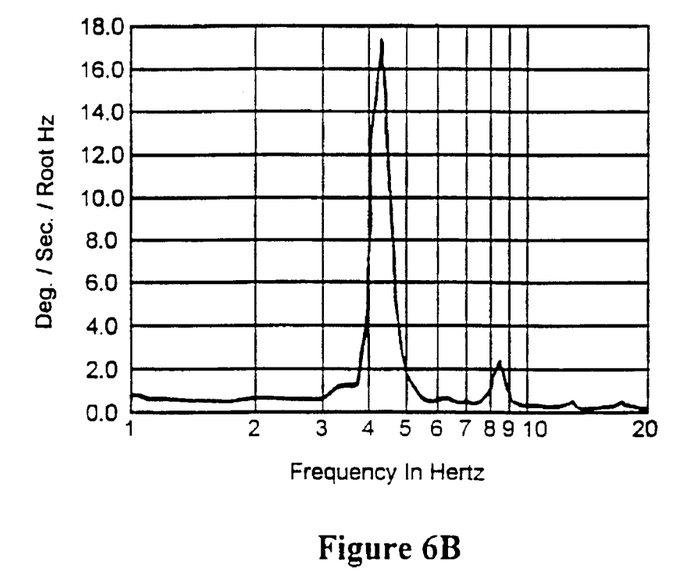
FIG. 6B is a power spectral density plot showing a characteristic frequency distribution signature of the tremor measured in FIG. 6A.

FIG. 6B is a plot of the power spectral density (degrees per second per root Hertz) of the hand tremor as a function of frequency (Hertz). This plot is derived from the data used in the plot of FIG. 6A. FIG. 6B shows Parkinson's characteristic signature with a dominant peak at 4.3 Hertz. In this case, the peak magnitude is low, and equal to 17.5 degrees per second per root Hertz. There is also a small resonance peak at 8.5 Hertz.

Figure 7A:
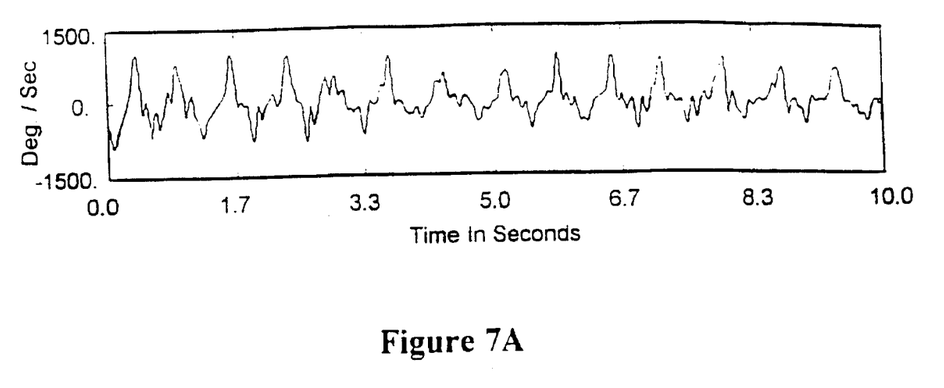
FIG. 7A illustrates a plot of angular rate versus time for a rotating arm, that is, for a pronation/supination test.

FIG. 7A is a plot of the angular rate (degrees/second) of an individual's hand as a function of time (seconds) when his entire arm is held vertical and rotated as if to screw in a light bulb as quickly as possible. This pronation/supination test conducted over, for example, a ten second time period helps a neurologist evaluate a patient's condition. Because Parkinson's disease is often indicated by cog wheeling or racheting during such tests, the plot of FIG. 7A assists the physician in visualizing and quantifying the extent of the disability.

Figure 7B:
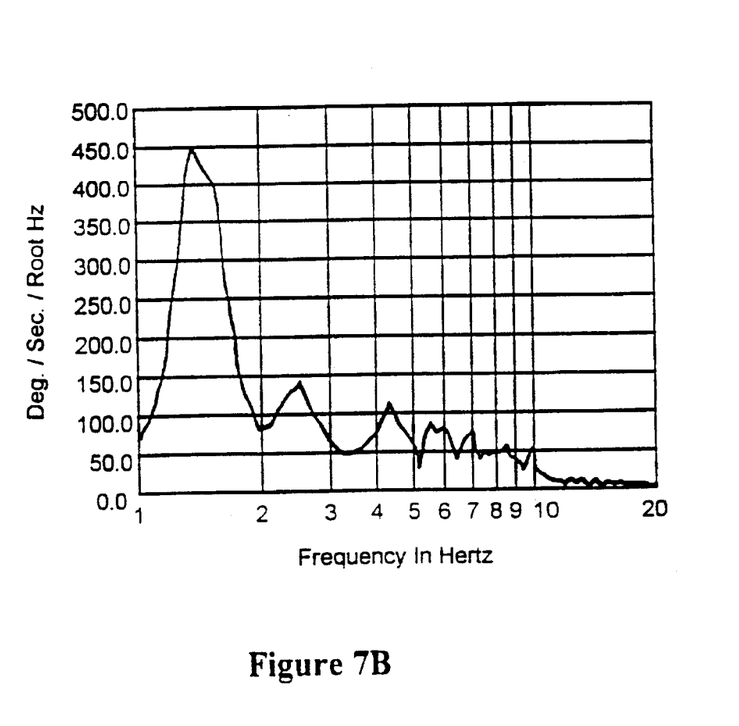
FIG. 7B is a power spectral density plot showing a characteristic frequency distribution signature of the same rotating arm measured in FIG. 7A.

FIG. 7B is a plot of the power spectral density (degrees per second per root Hertz) of the pronation/supination motion as a function of frequency (Hertz). This plot is derived from the data used in the plot of FIG. 7A and shows a peak frequency of 1.37 Hertz. This plot can be used to interpret the extent of the disability since the more advanced stages of neurological disorders reduce the peak magnitude, broaden the peak (i.e. reduce Q), and lower the frequency of the peak.

The data can be displayed on a computer monitor. In addition, a hard copy of the data can be provided by a portable inkjet printer 64 having preferably 300 dpi resolution such as Hewlett Packard Corporation inkjet printer Model No. 310. Additionally, the test data can be stored on a hard disk drive and/or a floppy disk drive so that the data can be easily transported to another location. This data can include a real time plot of angular rate versus time, a plot of the power spectral density versus frequency which typically goes to 20 Hertz on a log scale, individual parameters such as peak frequency, peak magnitude, Q, and angular displacement. Space can be provided in the graphical display for indicating the patient's data including name, age, sex, and background.

In operation, the present invention has numerous applications. For example, the systems and methods can quantify tremor associated with Parkinson's Disease, Huntington's Disease, Tourette's Syndrome, Essential Tremor, and Dystonias. The present invention can be even used to detect preclinical nonvisible tremors which may permit early treatment of various diseases.

In one application, the present invention can be used to quantify gait. A person's body will rock back and forth when walking as the feet are alternately weighted and unweighted. In one embodiment, the gyroscope is attached to the head or shoulder of the person with its sensitive axis pointing in the direction that the person is walking. Differences between a normal gait and a shuffle which may be indicative of Parkinsonism are not only easily seen but can be quantified in real time and in the frequency domain. This is useful in evaluating not only Parkinsonism, but also in judging if a person not having Parkinson's disease is an unsteady walker and likely to be injured in a fall. This can help identify if a person needs a greater level of attention, for example, at a health care facility.

Furthermore, the present invention can quantify movement disorders, such a Myoclonus, Choreoathetosis, Tardive Dyskinesia and other atypical tremors. The invention can quantify physician induced movement tests associated with the above diseases. Often a neurologist will instruct a patient to perform specific movements and visually observe irregularities. This aspect of the invention allows the physician to obtain quantitative information on such typical tests as pronation and supination of the arm.

In still another application, the present invention provides a system that detects and quantifies the side-effects of certain psychotropic drugs associated with the treatment of depression and other mental illnesses. These side-effects are often Parkinson-like tremors that are irreversible if not detected early enough to change the prescribed medication.

In another embodiment, additional gyroscopes are used to cross correlate motion at different locations of the body. For example, when a person with Parkinson's disease walks, his arms often swing differently from that of a person without the disease. The magnitude of the swing of the left arm is different from that of the right arm and can give a neurologist an additional diagnostic capability. In another example, one or more gyroscopes are used in the operating room during a procedure known as a thalamotomy. In this case, the neurosurgeon destroys a selected portion of the thalamus for relief of pain and involuntary movements. The real time plot of angular rate (tremor magnitude) versus time from the gyroscope allows the surgeon to locate the exact spot to minimize tremor.

Once the motion has been quantified, a medical professional can see the continuous, daily or monthly trends. Thus, a physical therapist can evaluate a patients' rehabilitation and their extremity's range of motion capability. In another example, a physician can monitor the effect of medication on the tremor of a Parkinson's patient over time. Additionally, one physician's data can be directly compared to another's data obtained at a different location or at a different time. Subjective comparisons are eliminated and real trends can be established. The present invention provides a unique signature of the individual's motion; and a signature that is obtained in a non-invasive, quick and simple manner.

A person using the present invention will find that it is accurate, easy to learn and operate, does not require a physician's presence, and is non-invasive. Typically, tests can be completed in only ten minutes including the steps of data processing and printing. No daily calibration effort is needed on the computer, system module or gyroscope. Since the computer based system embodiment is portable, screening tests for Parkinsonism and other neurological diseases can be easily conducted in the field. Likewise, because the system is portable, one system can be shared between users at different locations.

Those of ordinary skill in the art will appreciate that many variations in the foregoing embodiments are possible which remain well within the scope of the present invention. For example, the present invention also encompasses any system having a gyroscope and another type of sensor, such as an accelerometer, or including other types of gyroscopes, other types of signal analyzers or computer based systems, including application software, other regulated power supplies, or other types of displays of the quantified motion. The scope of the present invention must be determined in accordance with the appended claims.

What is claimed is:

1. A system for quantifying neurological function, comprising:

a gyroscope for sensing the angular rate of human or animal neurological movement disorders and producing an output signal indicative of the movement; and a signal analyzer for analyzing the output signal.

2. The system of claim 1, further comprising a power supply for the gyroscope.

3. The system of claim 1, further comprising means for attaching the gyroscope to a human or animal at a first location.

4. The system of claim 1, wherein the signal analyzer includes a Fast Fourier Transform spectrum analyzer.

5. The system of claim 1, wherein the signal analyzer includes means for permanently displaying the analyzed output signal.

6. The system of claim 1, further comprising a low pass filter set at about 30 Hertz and wherein the gyroscope has a frequency response from DC to at least 30 Hertz.

7. The system of claim 1, further comprising a second gyroscope for sensing the angular rate of a second motion of the human or animal at a second location and producing a second output signal indicative of the second motion.

8. The system of claim 7, wherein the signal analyzer compares the first and the second output signal.

9. The system for quantifying neurological function, comprising:

a gyroscope for sensing the angular rate of human or animal neurological movement disorders and producing an output signal indicative of the movement;

a power supply for the gyroscope; and a computer for analyzing the output signal.

10. The system for quantifying neurological function, comprising:

a gyroscope for sensing the angular rate of human or animal neurological movement disorders and producing an output signal indicative of the movement;

a computer for analyzing the output signal; and a system module for supplying power to the gyroscope and for conditioning the output signal.

11. The system of claim 10, wherein the output signal from the gyroscope is an analog signal and further comprising an analog to digital converter for converting the conditioned output signal to a digital signal.

12. The system of claim 10, wherein the system module includes a display of the real time angular rate of the motion being sensed.

13. The system of claim 10, wherein the system module includes an infrared sensor and the system includes an infrared remote controller spaced from the system module permitting remote control of the system.

14. The system of claim 10, wherein the computer provides power to the system module which resides within a disk drive bay in the computer.

15. The system of claim 10, wherein the computer includes software to quantify the motion by providing angular motion relations selected from the group consisting of the angular rate of the motion as a function of time, the power spectral density, the sharpness of resonance, the angular displacement of the motion, the peak frequency and peak magnitude of the power spectral density.

16. The system of claim 10, further comprising:

a monitor and/or printer for displaying a representation of the motion based on the analyzed output signal; and a hard drive and/or floppy drive for data storage.

17. A method of quantifying human or animal motion, comprising the steps of:

attaching a gyroscope to a human or animal;

sensing the angular rate of a neurological movement disorder of the human or animal with the gyroscope and producing an output signal indicative thereof; and quantifying the output signal.

18. The method of claim 17, further comprising the steps of filtering the output signal to reduce noise at higher frequencies.

19. The method of claim 17, further comprising the step of computing, based on the quantified output signal, an angular motion relation selected from the group consisting of the angular rate of the motion as a function of time, the power spectral density, the sharpness of resonance, the angular displacement of the motion, the peak frequency and peak magnitude of the power spectral density.

20. The method of claim 19, further comprising the steps of storing and displaying the angular motion relations.

21. The method of claim 17, further comprising the steps of displaying and storing test subject and operator background data.

22. The method of claim 17, further comprising:

measuring the angular rate of motion by simultaneously using more than one gyroscope; and evaluating phase and magnitude relationships between the gyroscopes.

23. A method of quantifying neurological function, comprising using a gyroscope for sensing the angular rate of human or animal neurological movement disorders and producing an output signal indicative of the movement.

* * * * *